US012661364B2

(12) United States Patent
Bezuglov et al.

(10) Patent No.: US 12,661,364 B2
(45) Date of Patent: Jun. 23, 2026

(54) REMEDY FOR HAIR GROWTH ENHANCING

(71) Applicant: GURUS BIOPHARM INC., Claymont, DE (US)

(72) Inventors: Vladimir Vilenovich Bezuglov, Moscow (RU); Igor Viktorovich Serkov, Chernogolovka (RU); Igor Ivanovich Lyubimov, Obolensk (RU); Igor Yuryevich Teterin, Moscow (RU); Nataliya Mikhailovna Gretskaya, Moscow (RU)

(73) Assignee: KOFF INVESTMENTS LLP, London (GB)

(*) Notice: Subject to any disclaimer, the term of this patent is extended or adjusted under 35 U.S.C. 154(b) by 852 days.

(21) Appl. No.: 17/623,573

(22) PCT Filed: Jun. 28, 2019

(86) PCT No.: PCT/RU2019/000470

§ 371 (c)(1),
(2) Date: Dec. 28, 2021

(87) PCT Pub. No.: WO2020/263115

PCT Pub. Date: Dec. 30, 2020

(65) Prior Publication Data

US 2022/0249514 A1 Aug. 11, 2022

(51) Int. Cl.

| | |
|---|---|
| ***A61K 31/5575*** | (2006.01) |
| ***A61K 31/197*** | (2006.01) |
| ***A61K 31/375*** | (2006.01) |
| ***A61K 31/455*** | (2006.01) |
| ***A61K 47/02*** | (2006.01) |
| ***A61K 47/10*** | (2017.01) |
| ***A61K 47/22*** | (2006.01) |
| ***A61K 47/26*** | (2006.01) |
| ***A61K 47/32*** | (2006.01) |
| ***A61K 47/36*** | (2006.01) |
| ***A61P 17/14*** | (2006.01) |

(52) U.S. Cl.
CPC ........ *A61K 31/5575* (2013.01); *A61K 31/197* (2013.01); *A61K 31/375* (2013.01); *A61K 31/455* (2013.01); *A61K 47/02* (2013.01); *A61K 47/10* (2013.01); *A61K 47/22* (2013.01); *A61K 47/26* (2013.01); *A61K 47/32* (2013.01); *A61K 47/36* (2013.01); *A61P 17/14* (2018.01)

(58) Field of Classification Search
CPC .............. A61K 31/5575; A61K 31/197; A61K 31/375; A61K 31/455; A61K 47/02; A61K 47/10; A61K 47/22; A61K 47/26; A61K 47/32; A61K 47/36; A61P 17/14
See application file for complete search history.

(56) References Cited

U.S. PATENT DOCUMENTS

| | | | | |
|---|---|---|---|---|
| 5,625,083 A * | 4/1997 | Bezuglov | .............. C07C 405/00 549/467 |
| 5,670,643 A | 9/1997 | Davis et al. | |
| 6,262,105 B1 | 7/2001 | Johnstone | |
| 12,012,375 B2 * | 6/2024 | Bezuglov | ................ A61P 27/06 |
| 2008/0241078 A1 * | 10/2008 | DeLong | ................... A61K 8/46 424/45 |

FOREIGN PATENT DOCUMENTS

| | | | |
|---|---|---|---|
| RU | 2 363 471 | 4/2009 | |
| RU | 2 481 339 | 12/2011 | |
| RU | 2 662 099 | 7/2018 | |
| WO | 1988/007362 | 10/1988 | |
| WO | 1995/010284 | 4/1995 | |
| WO | 1998/010284 | 3/1998 | |
| WO | 1999/053923 | 10/1999 | |
| WO | 2011/014649 | 7/2010 | |
| WO | 2014/158373 | 10/2014 | |
| WO | WO-2015176161 A1 * | 11/2015 | .............. A61P 17/14 |

OTHER PUBLICATIONS

International Search Report for PCT/RU2019/000470, mailed Apr. 19, 2020, 2 pages.
Written Opinion of the ISA with English Translation for PCT/RU2019/000470, mailed Apr. 19, 2020, 9 pages.
Serkov I.V. et al., "1, 3-Dinitrates of Cyclooxygenase Metabolites of Endocannabinoid 2-Arachidonoylglycerol Synthesis and Properties", Russian Journal of Bioorganic Chemistry, vol. 35 No. 2., 2009, pp. 225-232.
Blume-Peytavi, MD, et al., "A randomized double-blind placebo-controlled pilot study to assess the efficacy of a 24-week topical treatment by latanoprost 0.1% on hair growth and pigmentation in healthy volunteers with androgenetic alopecia", Journal American Academy of Dermatology, vol. 66, No. 5, May 2012, pp. 794-800.
(Continued)

*Primary Examiner* — Andrew D Kosar
*Assistant Examiner* — Phillip Matthew Rzeczycki
(74) *Attorney, Agent, or Firm* — Nixon & Vanderhye PC

(57) ABSTRACT

The invention relates to the field of cosmetology, dermatology and medicine, and is concerned with the development and production of a combination, and also of a composition based thereon, for hair growth enhancing in mammals and/or for preventing and/or treating alopecia, primarily in humans, and more particularly to combinations based on derivatives of F- and E-type prostaglandins, characterized by the absence of undesirable side-effects, and also to a stable composition comprising said combination. The use of a combination of prostaglandins in a single composition makes it possible to simultaneously activate a plurality of physiological processes, including stimulating a hair follicle to produce a new hair, increasing the local microcirculation in the area adjacent to the hair follicle, and reducing the aggregation of thrombocytes, thereby preventing thrombogenesis in the capillary network. Furthermore, the presence in the combination or in the composition based thereon of modified prostaglandins carrying a group of nitrogen oxide donors enables better penetration of other ingredients of the combination or composition into the skin.

16 Claims, 1 Drawing Sheet

(56) References Cited

OTHER PUBLICATIONS

Colombe et al., "Prostanoid receptors in anagen human hair follicles", Patterns of Expression, www.blackwellpublishing.com/EXD, Journal compilation Blackwell Munksgaard, Experimental Dermatology, Sep. 2007, pp. 17: 63-72.
Sugimoto et al., "Failure of Parturition in Mice Lacking the Prostaglandin F Receptor", Science, vol. 277, Aug. 1997, pp. 681-683.
Stjernschantz, "From PGF 2a-Isopropyl Ester to Latanoprost: A Review of the Development of Xalatan", cited in Investigative Ophtamology & Visual Science, vol. 42, No. 6, May 2001.
Roenigk, Jr., MD, "New Topical Agents for Hair Growth", Clinics in Dermatology, vol. 6, No. 4, Oct.-Dec. 1988, pp. 119-121.
Tanaka et al., "The effect of a synthetic 7-thiaprostaglandin E1 derivative, TEI-6122, on monocyte chemoattractant protein-1 induced chemotaxis in THP-1 cells", cited in British Journal of Pharmacology, No. 116, 1995, pp. 2298-2302.

* cited by examiner

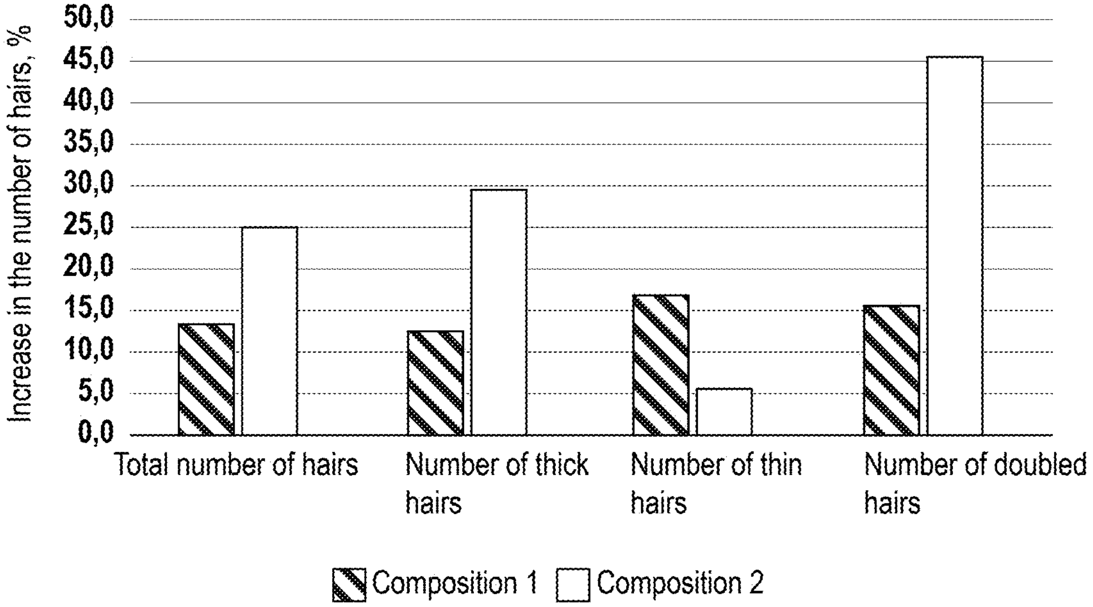
Increase in the number of hairs, %
50,0
45,0
40,0
35,0
30,0
25,0
20,0
15,0
10,0
5,0
0,0
Total number of hairs
Number of thick hairs
Number of thin hairs
Number of doubled hairs
Composition 1
Composition 2

REMEDY FOR HAIR GROWTH ENHANCING

This application is the U.S. national phase of International Application No. PCT/RU2019/000470 filed 28 Jun. 2019, which designated the U.S., the entire contents of each of which are hereby incorporated by reference.

FIELD OF THE INVENTION

The invention relates to the field of cosmetology, dermatology and medicine, and concerns the development and production of a combination, as well as a composition based thereon, for promoting hair growth in mammals, preferably in humans. More particularly, this invention relates to combinations, compositions and methods for stopping hair loss and/or restoring and activating hair growth.

BACKGROUND OF THE INVENTION

Baldness or alopecia is the process of partial or complete hair loss on the scalp. 9 out of 10 patients who come to see a trichologist complain of hair loss. There are several types of alopecia: alopecia areata, diffuse, androgenetic, cicatricial, seborrheic. Androgenic, the so-called male pattern alopecia, is the most common form of the disease. Studies show that 30-35% of the male population of the world aged 25 to 55 years is affected by androgenetic alopecia. In women, such hair loss is diagnosed somewhat less frequently.

Thanks to advances in medicine, causes of androgenetic alopecia have been clearly identified to date. The immediate cause of hair loss is the damaging effect of male hormones, androgens, on hair follicles located in the frontal and parietal regions. Under the influence of hormonal activity, the bulb having receptors that are sensitive to the hormone molecule gradually loses its ability to produce healthy hair and eventually dies, which leads to irreversible hair loss.

Despite the fact that hormonal activity is inherent in all men, only a third of them suffers from baldness, as mentioned above. This is due to the fact that the second key factor in the development of baldness is genetic information inherited by each person from his parents. It has been found that the baldness gene is inherited by a man through the maternal lineage in 70-72% of cases: the mother passes it on from her father to her son. In other cases, the baldness gene is inherited directly from the father. It is very rare that a man with androgenetic alopecia is the first in his family to be affected. Thus, the cause of hair loss is the symbiotic effect of two factors: heredity and hormonal activity.

Today, there are many ways to fight alopecia. For example, hair transplant is a non-pharmacological method. A hair transplant procedure is painful and expensive, in addition to the fact that it has a number of equally significant disadvantages. For example, the patient's own donor bulbs are often not sufficient to mask the problem area; with light and short hair, scars are visible on the back of the head after surgery, which cannot always be masked; the operation is often carried out in several stages, since the baldness area tends to increase, while the donor area is finite.

Other methods to fight baldness include exposure to ultraviolet radiation, massage, psychiatric treatment, and others. However, none of the above methods is considered effective. Revascularization surgery and acupuncture have also been shown to be poorly effective against alopecia.

Thus, the most common and promising approach to the problem is the development of a therapeutic agent for hair loss of various etiologies. Male pattern alopecia is considered the main indication for drug therapy. For a long time, the opinion was expressed that the systemic or topical application of an antiandrogenic hormone will provide the necessary inhibitory effect on the hair loss process, since the cause of male pattern baldness is an excess of androgens. However, studies did not support such a positive theory.

Testosterone was considered as an alternative. The androgenic hormone, testosterone, has been known, for example, to stimulate hair growth when applied topically to the deltoid region, as well as when administered into the chin and pubic region. It was found that even oral administration led to increased hair growth in the beard and the pubic region, as well as on the trunk and limbs. And although even topical application onto the arm causes increased hair growth, the hormone is ineffective on the scalp and can, on the contrary, lead to hair thinning High doses are also known of testosterone can cause male pattern baldness.

Currently, there are two drugs approved by the US FDA for the treatment of male pattern baldness: topical minoxidil (WO1999053923A1, WO1988007362A1 trademark ROGAINE® from Pharmacia & Upjohn), oral finasteride (WO1995010284A1, U.S. Pat. No. 5,670,643 trademark PROPECIA® from Merck & Co., Inc.). Despite the fact that the drugs are widely used in trichology, their insufficient effectiveness should be noted. As an example, the results of clinical studies can be cited: 19% of women who used 2% minoxidil noted moderate hair growth after 8 months of use, while 7% of women who took placebo had an identical result.

The search for more effective hair growth stimulants is ongoing due to safety concerns and the limited effectiveness of existing treatments. Phenytoin is one such drugs, which has an anticonvulsant effect and is widely used to control epileptic seizures. In children with epilepsy, hypertrichosis is common and usually appears 2-3 months after the start of therapy and first becomes noticeable on the extensor sides of the limbs, and then on the trunk and face. Streptomycin works in a similar way. After the discontinuation of the drugs, the hair density returns to the previous level and remains unchanged only in rare cases, i.e. hypertrichosis is triggered by the use of the above antibiotic.

There are treatment methods that show some promise in hair restoration in male pattern alopecia. Procedures include the application of a cream microemulsion containing estradiol and oxandrolone as active ingredients, as well as the use of organic silicon. However, unequivocal convincing results have not been achieved with estradiol treatment: the sensitivity to estradiol was different in different areas of the scalp, and due to undesirable side effects such as gynecomastia, estradiol must not be used at all in men, because very high topical doses are needed to obtain measurable hair growth effects.

The closest analogs of the described invention are prostaglandins, which have the same advantages as thyroid hormones, i.e., an increase in hair length and a change in pigmentation. Naturally occurring prostaglandins (eg., $PGA_2$, $PGB_2$, $PGE_1$, $PGE_2$, $PGD_2$, $PGF_{2a}$, and $PGI_2$) are cyclooxygenase metabolites of C-20 unsaturated fatty acids. $PGF_{2a}$, natural to the human body, is characterized by hydroxyl groups at the C9 and C11 positions on the cyclopentane ring, a cis double bond between C5 and C6, and a trans double bond between C13 and C14.

Natural prostaglandin F analogs are known in the art. For example, patent documents U.S. Pat. No. 4,024,179 (Substituted ω-pentanorprostaglandins, publication date 17 May 1977), U.S. Pat. No. 4,128,720 (Prostaglandin analogues, publication date 5 Dec. 1978), U.S. Pat. No. 4,011,262 (13,14-Dihydro-15-substituted-ω-pentanorprostaglandins of the two series, publication date 8 Mar. 1997) U.S. Pat. No. 3,776,938 (Dihydro-pgel, publication date 4 Dec. 1973), RU2481339 (Substituted cyclopentanes with prostaglandin activity, publication date 10 May 2013). U.S. Pat. No. 6,262,105 (Method of enhancing hair growth, publication date 17 Jul. 2017) notes that prostaglandins and their derivatives can be used to promote hair growth.

To date, it has now been found that bimatoprost (RU2363471C2), trade name Lumigan (Allergan Inc., Irvine, CA, USA), an ophthalmic solution for the treatment of glaucoma, is able to effectively enhance eyelash growth. In addition, Allergan Inc. clinical trials are conducted for the indication of male pattern alopecia using bimatoprost.

Pilot double-blind clinical studies were conducted to investigate the effect of one of the commercial drugs for the treatment of glaucoma, latanoprost, on the activation of scalp hair growth. Previous numerous clinical observations showed that latanoprost promotes eyelash growth, which was noted as an adverse reaction in the treatment of glaucoma, manifesting when the drug comes into contact with the eyelids. In a clinical study, a significant increase in hair density was noted due to both terminal and vellus hair after 24 weeks of application of 0.1% latanoprost to the scalp. It has been concluded that latanoprost may be useful in stimulating hair follicle activity and treating hair loss (J Am Acad Dermatol. 2012 May; 66 (5):794-800).

Loreal conducted studies of the effect of various prostaglandins on hair follicle activation and found that several prostaglandins are involved in the regulation of hair growth, not only prostaglandin $F_{2a}$ (Experimental Dermatology 2008; 17: 63-72). It has been noted that $PGF_{2a}$-FP receptor-deficient mice did not have fur problems (Science 1997: 277: 681-683). Indeed, as noted for $PGF_{2a}$ agonists, treatment with PGE2 also initiated hair regrowth in both mice (Invest Ophthalmol Vis Sci 2001:42: 1134-1145.) and humans (New topical agents for hair growth. Clin Dermatol 1988: 6: 119-121.). In this regard, it is notable that PGE2 EP1, EP2 and EP3 receptors were expressed in the dermal papilla (Experimental Dermatology 2008; 17: 63-72). Otherwise, the effect that promotes hair growth may be indirect, caused by the environment surrounding the hair follicle, as a result of activation of angiogenesis, correction of the extracellular matrix, or as a result of changes in the availability of growth factors. Therefore, not only PGF2a can participate in the regulation of hair growth, but also other PGs, in particular $PGE_1$, $PGE_2$, $PGD_2$, etc. The zones of PG effect in the hair follicle can differ, and the activation of several receptors at once would significantly increase the activity of hair growth.

This can be easily explained since PGs generally have a wide range of biological activities. For example, PGE2 has the following important properties: a) regulates the proliferation of stem cells by activating the canonical WNT/β-catenin signaling pathway, which is key in the regeneration of any tissue b) regulates the synthesis of cytokines, c) regulates the immune response, and d) induces vasodilation. For example, vasodilation is thought to be one of the mechanisms by which minoxidil promotes hair growth. In vitro data in the literature also indicate some anti-inflammatory properties of prostaglandins (Br. J Pharm., 116, 2298, (1995)). However, previous attempts to use prostaglandins to stimulate hair growth have been unsuccessful. The analysis of study results made it clear that the main role in the activation of hair growth in the overwhelming number of studies was attributed to $PGF_{2a}$, which turned out to be not entirely correct, since, as it became clear later, PGE2 has an even stronger potential to stimulate hair growth due to the activation of bulb stem cells and further reduction of the molecule to $PGF_{2a}$, thus having a more complex and effective action. Different prostaglandin analogs can bind to a variety of receptors at different concentrations with a biphasic effect.

The use of prostaglandins, mainly $PGF_{2a}$ derivatives (since antiglaucoma drugs were developed on the basis of these prostaglandins and the first side effects in the form of hypertrichosis of the eyelashes, upper eyelids and eye area were observed) to inhibit hair loss and stimulate the growth of new hair has become such an irrefutable fact that application WO2011/014649 was submitted on the methods for inhibiting hair growth or depilation, based not on the activation of the $PGF_{2a}$-FP receptor, but on its inhibition by specific antagonists.

Thus, the wide range of applications of prostaglandins, as well as the interest in working with them worldwide indicates the promising nature of this field of research. Despite the fact that all of the above drugs are used on the market or are studied in certain stages of clinical trials, the limited effectiveness of these drugs as monotherapy is obvious.

SUMMARY OF THE INVENTION

The objective of the present invention is to develop a new effective medicinal product for hair growth enhancing and/or prevention and/or treatment of alopecia in a subject, based on prostaglandin F and E analogs.

The technical result of the invention is the development and production of a new effective and non-toxic combination of prostaglandin F and E derivatives for hair growth enhancing and/or prevention and/or treatment of alopecia, characterized by the absence of undesirable side effects, as well as a stable composition comprising said combination. The use of a combination of prostaglandins in one composition allows simultaneously activating a plurality of physiological processes, including stimulating a hair follicle to form new hair, enhancing the local microcirculation in the area adjacent to the hair follicle and reducing the aggregation of platelets and thereby preventing thrombogenesis in the capillary network. Furthermore, the presence of modified prostaglandins carrying a group of nitric oxide donors in the combination or composition based thereon promotes better penetration of other ingredients of the combination or composition into the skin.

The said technical result is achieved by developing and creating a combination for hair growth enhancing and/or prevention and/or treatment of alopecia in a subject, comprising at least a compound of formula (I) and a compound of formula (II) and/or formula (III), wherein the compound of formula (I) is:

Formula (I)

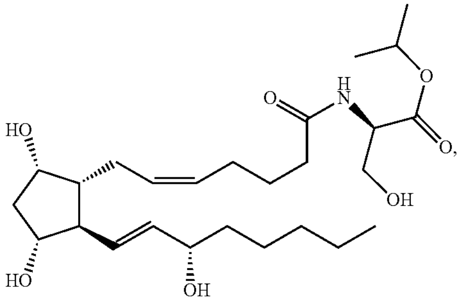, the compound of formula (II) is:

Formula (II)

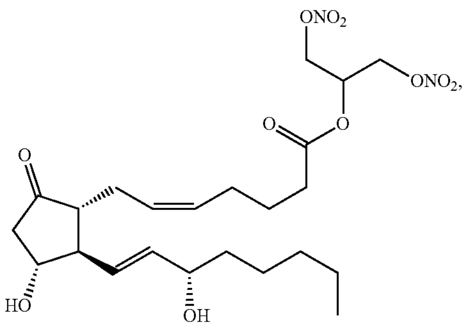

the compound of formula (III) is:

Formula (III)

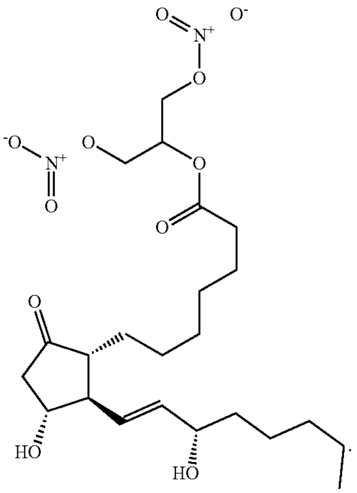

In particular embodiments of the invention, the combination of the invention comprises a compound of formula (I), formula (II) and formula (III).

In particular embodiments of the invention, the combination of the invention comprises a compound of formula (I) and formula (II).

In particular embodiments of the invention, the combination of the invention comprises a compound of formula (I) and formula (III).

In particular embodiments of the invention, alopecia is diffuse (female pattern), androgenetic, or alopecia areata.

The present invention also provides a composition for hair growth enhancing and/or prevention and/or treatment of alopecia, comprising a combination of the invention and at least one excipient. Moreover, the combination comprises components in an effective quantity.

In particular embodiments of the invention, the excipient is a carrier, filler and/or solvent.

In particular embodiments of the invention, the content of the compound of formula (I) in the combination is 50-300 μg per 1 mL of the finished composition of the invention.

In particular embodiments of the invention, the content of the compound of formula (II) in the combination is 50-300 μg per 1 mL of the finished composition of the invention.

In particular embodiments of the invention, the content of the compound of formula (III) in the combination is 50-200 μg per 1 mL of the finished composition.

The present invention also includes the use of the composition of the invention for hair growth enhancing and/or prevention and/or treatment of alopecia in a subject. In particular embodiments of the invention, alopecia is androgenetic, diffuse or alopecia areata.

In particular embodiments of the invention, the composition is applied topically.

In particular embodiments, the composition is used daily or every other day.

In particular embodiments of the invention, the subject is a human.

The present invention also includes the preparation of a combination and/or composition based thereon.

The invention also relates to a method of hair growth enhancing and/or prevention and/or treatment of alopecia in a subject.

As a result of the studies carried out, it was found that prostaglandin derivatives comprised in the combination of the invention and including NO donors and chemical structures that activate NO synthase more potently than prostaglandins themselves, have activity against the activation of hair follicles of both the scalp and bristly hair (eyelashes, eyebrows, etc. etc.) and show incredibly effective results. During studies, it was incidentally found that, in addition to the potent effect of strengthening and stimulation of hair growth, the molecules synthesized in this way facilitate the penetration of a medicinal product into the dermis, where the follicles and their regulatory receptors are located, the activation of which leads to hair growth. Prostaglandin derivatives with NO donors activate several mechanisms of action on the hair follicle, such as activation of hair bulb papilla stem cells, activation of physiological angiogenesis, activation of the extracellular matrix, improvement of blood rheology and facilitation of delivery of growth factors and other trace elements and vitamins through the restored capillary network of the hair follicle. The whole mechanism of action in totality leads to a potent effect of hair growth enhancing.

A complex (combination) of modified derivatives of prostaglandins F and E has been developed as an effective agent that enhances regeneration and hair growth in order to prevent baldness and for partial or complete restoration of the pelage at different stages of hair loss. The invention allows hair growth enhancing in humans and animals, and the developed method of enhancing is compatible with various types of therapeutic agents or carriers, therefore, can be combined with those that themselves exhibit some therapeutic activity, such as microemulsions, creams or topical compositions containing estradiol and oxandrolone, minoxidil or agents that block the conversion of testosterone to dihydrotestosterone, antiandrogenic agents that block androgen receptors, peptide and other growth factors. In addition, the invention aimed at treatment of baldness and of hair growth enhancing, while being effective for its intended purpose, is not toxic and does not cause undesirable side effects. This application provides a method for the treatment of alopecia in men or women, which can be used by a patient under the supervision of a physician with not more stringent requirements than those for other therapeutic agents applied topically. Unlike the above-mentioned analogs, the invention provides the treatment of alopecia with a female pattern of hair loss and androgenetic alopecia, which occurs in both men and women, as well as in the complex treatment of alopecia areata, and is safe, easy to use, painless, convenient for cosmetic use (does not cause discomfort to the subject and does not leave traces).

BRIEF DESCRIPTION OF DRAWINGS

FIG. 1. Comparative results of clinical and laboratory studies evaluating the efficacy of the composition of the invention by analyzing phototrichograms: Agent for hair growth of composition 1; Agent for hair growth of composition 2, obtained at the beginning and after 3 months of use.

DETAILED DESCRIPTION OF THE INVENTION

Definition and Terms

For a better understanding of the present invention, below are some of the terms used in the present description of the invention.

As used in the description of this invention, the terms "includes" and "including" are interpreted as meaning "includes but not limited". These terms are not intended to be interpreted as "consists only of".

The term "carrier" as used herein means one or more compatible substances that are suitable for administration to a mammal, preferably a human. For example, the carrier includes solid or liquid diluents, hydrotropes, surfactants, and encapsulating agents. The term "compatible" as used herein means that the components of the composition are miscible with the prostaglandin derivatives and with each other in such a way that there is no interaction that would significantly reduce the effectiveness of the composition under normal conditions of use. The carriers must have sufficiently high purity and sufficiently low toxicity to be suitable for use by the human to be treated. The carrier can be inert, have pharmaceutical or cosmetic advantages, or both.

The choice of a carrier depends on the method by which the active ingredients will be used and the form of the composition. The composition can be presented in various forms suitable for topical administration (for example, for topical application to the scalp and skin in the area of the eyes, excluding mucous membranes, delivery by liposomal systems, polymeric biodegradable (nano) particles, or iontophoresis). Local administration directly to the desired hair growth site is preferred.

Carriers typically contain one or more ingredients selected from the group consisting of: a) diluents, b) lubricants, c) binders, d) disintegrants, e) colorants, f) flavorings, g) sweeteners, h) antioxidants, i) preservatives, j) glidants, k) solvents, l) suspending agents, surfactants, m) penetration enhancers, n) combinations thereof, and others.

The compositions claimed in this invention contain a combination of this invention together with pharmaceutically acceptable carriers, which may include any solvents, diluents, dispersions or suspensions, surfactants, isotonic agents, thickening agents and emulsifiers, preservatives, binders, lubricants etc., suitable for a particular dosage form.

The compositions of the invention may further optionally include an activity-enhancing component. The specified component is preferably selected from the group consisting of hair growth enhancers I) (except for modified $PGF_{2\alpha}$ and $PGE_1/PGE_2$ with NO donors), including physiologically active substances, minerals and extracts of plant and animal tissues, and II) enhancers of the penetration of active substances through the skin, as well as various fillers, stabilizers and preservatives.

Component I) is an additional hair growth enhancers and can include but not be limited to vasodilators, antiandrogens, cyclosporins, cyclosporine analogs, antimicrobial, anti-inflammatory drugs, thyroid hormones, thyroid hormone derivatives, as well as thyroid hormone analogs, sex hormone analog preparations for correction of hormone status in postmenopausal women, non-selective prostaglandin agonists or antagonists, retinoids, triterpenes, and combinations thereof. Non-selective prostaglandin agonists or antagonists do not selectively activate the FP receptor and can activate other receptors such as prostanoid EP1-4, IP receptors or block DP1, DP2, TP receptors. Other suitable alternatives for component I) can include but not be limited to estradiol, chlorpheniramine maleate, chlorophyllin derivatives, cholesterol, salicylic acid, cysteine, methionine, red pepper tincture or capsaicin, benzyl nicotinate, D, L-menthol, peppermint oil, calcium pantothenate, panthenol, castor oil, prednisolone, resorcinol, chemical activators of protein kinase C, glycosaminoglycan chain cell uptake inhibitors, glycosidase activity inhibitors, glucosaminoglyconase inhibitors, pyroglutamic acid esters, six-carbon saccharinic acids or acylated six-carbon saccharinic acids, aryl-substituted ethylenes, N-acylated amino acids, flavinoids, ascomycin derivatives and analogs, histamine antagonists such as diphenhydramine hydrochloride, triterpenes such as carophylline and ursolic acid, proteoglycanase or glucosaminoglycanase inhibitors, estrogen agonists, and antagonists, promoters, analogs or inhibitors of cytokines and growth factors such as interleukin-1 and interleukin-6 inhibitors, interleukin-10 promoters, tumor necrosis factor inhibitors, vitamins such as vitamin D analogs and antagonists of parathyroid hormones, vitamin B12 analogs and panthenol, agonists and benzophenones, and hydantoin, anticonvulsants, such as phenytoin, and combinations thereof, interferon antagonists, hydroxy acids.

The most preferred enhancers of hair growth activity are minoxidil, finasteride, dutasteride, antiandrogen drugs such as androgen receptor blockers, sex hormone analog preparations and some peptide growth factors, if applicable for cosmetics.

Component II) is a penetration enhancer that can be added to all compositions. The quantity of component II) when present in the composition is generally from 1 to 5%. Examples of penetration enhancers include, but are not limited to, 2-methyl-propan-2-ol, propan-2-ol, ethyl 2-hydroxypropanoate, hexane-2,5-diol, polyoxyethylene (2) ethyl ester, di(2-hydroxypropyl) ester, pentane-2,4-diol, acetone, 2-hydroxypropionic acid, 2-hydroxyoctonic acid, propan-1-ol, 1,4-dioxane, tetrahydrofuran, butan-1,4-diol, propylene glycol dipelargonate, oleyl alcohol, lauryl alcohol, dioctyl adipate, adipic acid dicapryl ester, adipic acid diisopropyl ester, sebacic acid diisopropyl ester, dibutyl sebacate, diethyl sebacate, dimethyl sebacate, sebacic acid dimethyl ester, dioctylphthalate sebacate, suberic acid dibutyl ester, dioctylphthalate azelate, dibenzyl sebacate, dibutylphthalate, dibutyl azelate, myristic acid ethyl ester, dimethyl azelate, myristic acid butyl ester, dibutyl succinate, didecyl phthalate, decyl oleate, ethyl caproate, salicylic acid ethyl ester, isopropyl palmitate, ethyl laurate, 2-ethyl-hexyl pelargonate, isopropyl isostearate, butyl laurate, benzyl benzoate, butyl benzoate, hexyl laurate, capric acid ethyl ester, caprylic acid ethyl ester, butyl stearate, salicylic acid benzyl ester, 2-hydroxypropanoic acid, N,N-dimethylacetamide, N,N-dimethylformamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfuryl alcohol, urea, diethyl-m-toluamide, 1-dodecylazacycloheptan-2-one, omega-3 fatty acids, and fish oil, and combinations thereof.

Fillers, stabilizers, and preservatives include, but are not limited to, benzalkonium chloride, benzethonium chloride, phenol, polyoxyethylene (2) methyl ester, propylene glycol dipelargonate, polyoxypropylene 15 stearyl ester, octyl alcohol, polyoxyethylene oleyl alcohol ester.

An effective quantity of the components of the combination or composition of the invention means the quantity of a compound delivered to a patient such that the patient is most likely to exhibit the desired response to treatment (prophylaxis). The exact quantity required may vary from subject to subject depending on the age, body weight and general condition of the patient, the severity of the disease/condition, combination treatment with other drugs, etc.

The combination or composition based thereon can be administered to a patient in any quantity effective for the treatment or prevention of alopecia and/or for promoting hair growth. When the combination of the invention is used as part of a combination therapy regimen, the dose of each of the combination therapy components is administered over the desired treatment period. The compounds comprising the combination therapy can be administered to a patient both simultaneously, as a dosage containing all the components and as individual dosages of the components.

Use of the Object of the Invention

A method of using an object of the invention includes administering to a mammal (preferably a human) suffering from hair loss a composition comprising a combination of the modified prostaglandin derivatives of the invention. Preferably topical application of a composition comprising a combination of modified prostaglandin derivatives. More preferably, the composition is a composition containing A) a complex (combination) of modified prostaglandin derivatives, B) a carrier, and C) an additional activity enhancer.

Surprisingly, it has been found that, as a result of the use of modified prostaglandin derivatives in the compositions and methods of the present invention, hair tends to thicken and darken, while hair graying is likely to be reversed. The method includes application of a topical composition to growing hair and skin at a growing hair site. In a particular embodiment of the present invention, a topical composition, in particular an eyelash and eyebrow agent, is applied to the eyelashes and eyebrows.

The administered dosage of a combination of various types of modified prostaglandin derivatives in one (1) mL of the finished cosmetic or topical dosage form for topical application of a prostaglandin $F_{2a}$ derivative is usually 0.01 mg to 0.3 mg, preferably 0.1 mg to 0.2 mg, more preferably 0.075 mg to 0.15 mg; for a prostaglandin $E_1$ derivative is 0.01 mg to 0.15 mg, preferably 0.025 mg to 0.125 mg, more preferably 0.05 mg to 0.1 mg; for a prostaglandin $E_2$ derivative is 0.01 mg to 0.3 mg, preferably 0.025 mg to 0.15 mg, more preferably 0.05 mg to 0.15 mg. The ratio of prostaglandin derivatives in a series of prostaglandin $F_{2a}$-$E_2$-$E_1$ derivatives is preferably 3-3-1.

The composition of the invention comprising a combination of prostaglandin derivatives is applied topically daily or every other day for a relatively short period (eg., several weeks). Typically, 10 to 12 weeks is sufficient for the first visual result, usually on a phototrichogram. A full course can last several months, usually up to 6. Compositions for topical application are preferably unwashable. The topical composition should not be removed from the treated area for at least several hours after application. The above described embodiments, including dose ranges, are only exemplary, and daily administration can be adjusted depending on various factors. The specific dose of prostaglandin derivatives for topical application, as well as the duration of treatment, the relevance of topical or additional systemic treatment are interdependent. The strength and treatment regimen will also depend on factors such as the particular combination of prostaglandin derivatives used, indications for treatment, individual characteristics (weight, age, sex and medical condition of the subject), adherence to the treatment regimen, and the presence and severity of side effects of treatment.

The object of the invention comprises from two to three basic compounds (prostaglandin derivatives) in the composition, namely, a prostaglandin $F_{2a}$ derivative, a prostaglandin $E_2$ derivative and/or a prostaglandin $E_1$ derivative with NO donors in the molecule. The composition may further include a compatible component such as, for example, a carrier and/or one or more additional activity enhancers.

In a preferred embodiment of the invention, the combination of prostaglandin derivatives is applied topically. Topical compositions that can be applied topically to the skin can be in any form including solution, oil, serum, cream, ointment, gel, lotion, shampoo, hair conditioner, milk, cleanser, moisturizer, spray, etc.

Topical compositions include: component A) modified derivatives of natural prostaglandins described above and component B), in particular a carrier. The carrier of the topical composition preferably facilitates the penetration of prostaglandins into the skin to enter the environment of the hair follicle. Compositions for topical application may preferably further contain component C), one or more additional activity enhancing components, as described above.

The topical composition preferably further comprises 1 to 20% of component C), as well as a sufficient quantity of component B), so that the quantities of components A), B) and C) are combined to give 100%. The quantity B) of the carrier used in combination with prostaglandins is sufficient to provide a practical quantity of the composition to be administered per standard dose of the compound.

Component C) is an optional activity enhancer as described above. Any of hair growth stimulants I) and II) penetration enhancers can be added to the topical composition. Preferably topical compositions comprise from 0.01 to 15% of component I) of the additional hair growth stimulant. More preferably, the composition comprises from 0.1 to 10%, and most preferably from 0.5 to 5% of component I). Preferably, the topical composition comprises from 1 to 5% of component II).

Prostaglandin derivatives can be included in a kits containing combinations of the objects of the invention in topical compositions; information and/or instructions that will indicate how to use the kit for hair growth enhancing and/or treatment and/or prevention of alopecia in a mammal, preferably a human Information and instructions can be textual descriptions and/or figures and/or diagrams. In addition, in an alternative embodiment, the kit may include prostaglandin derivatives and/or the composition, and information and/or instructions regarding methods of application of the combination and/or composition for hair growth enhancing and/or treatment and/or prevention of alopecia in a subject.

Thus, the invention provides a new highly effective preparation of the above combinations for hair growth enhancing and/or treatment and/or prevention of alopecia, in particular male pattern alopecia. The invention promotes increased metabolism, improved blood circulation, saturation of hair roots with vitamins. In some particular embodiments of the invention, the preparation of the invention has a preferably gel-like consistency, which contributes to its effective distribution and penetration through the skin barrier, and has a positive effect on the metabolic processes of the skin, not only of the superficial layers, but also of the deep ones.

The use of the invention allows expanding the arsenal of pharmaceutical and cosmetic agents for stimulation of hair growth and/or treatment and/or prevention of alopecia.

DESCRIPTION OF EMBODIMENTS

The Procedure for Preparing a Compound of Formula (I)—Amide of Prostaglandin $F_{2alpha}$ and L-serine Isopropyl Ester, ((R)-isopropyl 2-((Z)-7-(1R,2R,3R,5S)-3,5-dihydroxy-2-((8,E)-3-hydroxyoct-1-en-1-yl)cyclopentyl)hept-5-enamide)-3-hydroxypropanoate)

1880 μL of triethylamine (13.6 mmol) were added to a solution of 3750 mg (10.6 mmol) of prostaglandin $F_{2alpha}$ in 50 mL of acetonitrile at room temperature, stirred for 5 min, and then 1769 μL (13.6 mmol) of isobutyl chloroformate were added. It was stirred for 40 min at room temperature. 2600 mg (13.6 mmol) of L-serine isopropyl ester hydrochloride were dissolved in 8 mL of water, 2900 μL (21 mmol) of triethylamine were added, and the resulting solution was added dropwise to the above solution of mixed anhydride with stirring and cooling to 4-8° C. The reaction mixture was stirred for 40 min while cooling to 4-8° C. Acetonitrile was carefully removed from the solvent mixture on a rotary evaporator, the residue was diluted with ethyl acetate (500 mL), washed with water (2×50 mL) and saturated sodium chloride solution (1×50 mL). The organic extract was pooled and dried over anhydrous sodium sulfate, then evaporated on a rotary evaporator and dried in an oil pump vacuum.

The yield was 4730 mg (92%) as an oil that solidifies at cold temperatures (+4° C.).

$^1$H-NMR ($CDCl_3$): 0.89 (3H), 1.22 (6H), 1.3 (9H), 1.76 (3H), 2.04 (6H), 2.39 (2H), 3.9 (2H), 4.03 (2H), 4.13 (1H), 4.63 (1H), 5.08 (1H), 5.45 (4H), 6.83 (1H). $[\alpha]_D^{25}$=28.4°, c=1, EtOH.

IR spectrum (film of substance): 1732 $cm^{-1}$ (carbonyl ester), 1653 (amide carbonyl), 2935, 2980 and 1455 $cm^{-1}$, (stretching and deformation vibrations of alkyl groups), 3360 $cm^{-1}$ (br. stretching vibrations of OH groups).

Compounds of formula (II) ((Z)-1,3-bis(nitroxy)propanyl-2-7-((1R,2R,3R)-3-hydroxy-2-((S,E)-3-hydroxyoctene-1-yl-1)-5-oxocyclopentenyl)-5-heptenoate) and formula (III) ((Z)-1,3-bis(nitroxy)propan-2-yl-7-((1R,2R,3R)-3-hydroxy-2-((S,E)-3-hydroxyoct-1-en-1-yl)-5-xocyclopentyl) heptanoate) can be prepared according to the procedures described in U.S. Pat. No. 5,625,083 (publication date: 29 Apr. 1997).

Example of Preparation of a Combination (Combination 1) Based on Prostagladins of the Invention To prepare the combination of the invention, take an appropriate quantity of each prostaglandin: amide of prostaglandin $F_{2alpha}$ and L-serine isopropyl ester (compounds of formula (I), prostaglandin $E_2$ dinitroglycerin ester (compounds of formula (II), prostaglandin $E_1$ dinitroglycerin ester (compounds of formula (III)—in the following ratio (by weight) 3:3:1).

To prepare 20 kg of a cosmetic composition for stimulation of hair growth, take 3 g of prostaglandin $F_{2alpha}$ amide and L-serine isopropyl ester, 3 g of prostaglandin E2 dinitroglycerin ester and 1 g of prostaglandin $E_1$ dinitroglycerin ester. Store these prostaglandins dissolved in isopropyl alcohol (for prostaglandin F2) or 95% ethyl alcohol (for prostaglandins E) at a concentration of 100 mg/mL. Place the calculated quantity of a solution of each of the components in weighed flasks and remove the solvent under vacuum to a constant weight of the residue. In case of a shortage, add the required quantity of the original prostaglandin solution. Add 50 mL of ethyl alcohol in each flask to achieve complete dissolution of the component and quantitatively transfer the solution into a 250 mL flask. Evaporate to dryness under vacuum. Dissolve the residue in 600 mL of ethoxydiglycol. Use the resulting clear solution comprising combination 1 to prepare a composition for stimulation of hair growth.

Example of a Composition of the Invention

The formulation of a hair serum (example of composition 1 of the invention) in addition to the combination of modified prostaglandin derivatives in the form of:

- amide of prostaglandin $F_{2alpha}$ and L-serine isopropyl ester (compound of formula (I))—0.015%,
- prostaglandin $E_2$ dinitroglycerin ester (compound of formula (II))—0.015%,
- prostaglandin $E_1$ dinitroglycerin ester (compound of formula (III))—0.005%,
- in a 3:3:1 ratio may include, by way of example, the following components as % w/w in the form of a carrier:

| | |
|---|---|
| 1,3-Propanediol | 4 |
| Ethoxydiglycol | 3.1995 |
| Complex of bioactive components (Niacinamide, Calcium Pantothenate, Sodium Ascorbyl Phosphate, Tocopheryl Acetate, Pyridoxine HCl, Maltodextrin, Silica, Sodium Starch Octenylsuccinate) | 1 |
| Polyquaternium - 37 | 1 |
| Sodium hydroxide | 0.07 |
| Phenoxyethanol, Glyceryl Laurate | 0.8 |
| Polysorbate 20 | 1.5 |
| Methylisothiazolinone | 0.05 |
| Water (GOST R 51232-98) | q.s. to 100% |

The formulation of the serum for eyelash strengthening and growth (example of composition 2 of the invention) may include, in addition to the following modified prostaglandin derivatives:

- amide of prostaglandin $F_{2alpha}$ and L-serine isopropyl ester (compound of formula (I))—0.015%,
- prostaglandin $E_1$ dinitroglycerin ester (compound of formula (III))—0.005%, in a 3:1 ratio, by way of example, the following components as % w/w in the form of a carrier:

| | |
|---|---|
| 1,3-Propanediol | 4 |
| Ethoxydiglycol | 3.1995 |
| Dipotassium glycyrrhizate | 0.5 |
| Sodium hyaluronate crosspolymer/Pentylene glycol/Water | 0.8 |
| Ammonium acryloyldimethyltaurate | 0.8 |

-continued

| | |
|---|---|
| vinylpyrrolidone (VP) copolymer | |
| 10% sodium hydroxide solution | 0.07 |
| Phenoxyethanol, Glyceryl Laurate | 0.8 |
| Polysorbate 20 | 1.5 |
| Methylchloroisothiazolinone, methylisothiazolinone | 0.05 |
| Water (GOST R 51232-98) | q.s. to 100% |

The formulation of the serum for eyebrow strengthening and growth (example of composition 3 of the invention) may include, in addition to the following modified prostaglandin derivatives:

amide of prostaglandin $F_{2alpha}$ and L-serine isopropyl ester (compound of formula (I))—0.015%, prostaglandin $E_1$ dinitroglycerin ester (compound of formula (III))—0.005%, by way of example, the following components as % w/w in the form of a carrier:

| | |
|---|---|
| 1,3-Propanediol | 4 |
| Ethoxydiglycol | 3.1995 |
| Dipotassium glycyrrhizate | 0.5 |
| Sodium hyaluronate crosspolymer/Pentylene glycol/Water | 0.8 |
| Propylene glycol, water, onion extract" | 1 |
| Ammonium acryloyldimethyltaurate VP copolymer | 0.8 |
| 10% sodium hydroxide solution | 0.07 |
| Phenoxyethanol, Glyceryl Laurate | 0.8 |
| Polysorbate 20 | 1.5 |
| Methylchloroisothiazolinone, methylizothiazolinone | 0.05 |
| Water (GOST R 51232-98) | q.s. to 100% |

Stability Analysis of Cosmetic Compositions with Various Formulations of the Invention During Accelerated Storage at Room Temperature The cosmetic composition for stimulation of hair growth (example of composition 1 according to the invention, see above) was held at +25-27° C. for 2 months. Samples were taken every week and analyzed for the content of the components of the combination by HPLC. To prepare a sample for analysis, 1 g of gel was taken from the cosmetic composition into a round-bottom glass centrifuge tube and 2 g of distilled ethyl acetate were added. The mixture was shaken on a Multi-Vortex V32 until the liquids were completely mixed for 3 min. The resulting suspension was centrifuged for 5 min at 6000 rpm for complete separation of the layers. The upper layer (ethyl acetate layer) was carefully removed with a glass pipette and transferred to a conical-bottom flask (V25 mL). Another 2 g of distilled ethyl acetate were added to the solution remaining in the test tube, and the extraction procedure was repeated once again. The upper layer (ethyl acetate layer) was carefully removed with a glass pipette and added to the previously collected solution. The organic layer was evaporated on a rotary evaporator and dried in an oil pump vacuum. The residue was dissolved in ethanol to obtain a solution with an ethanol concentration of 26 mg/100 μL. The extract was analyzed by microcolumn reversed-phase HPLC in an acetonitrile-water gradient system (linear gradient, 5→100% acetonitrile). The components of the combination of the invention were identified by comparison with reference standards. The quantity of each component was estimated by the signal area in the chromatogram.

The results are presented in the table.

TABLE 1

The content of modified prostaglandin $F_2$ in the cosmetic composition for stimulation of hair growth (as % to the initial one) when stored at room temperature.

| Hold time, weeks | Prostaglandin $F_2$ content, %* | Ratio of prostaglandins $F_2$-$E_2$-$E_1$ in combination |
|---|---|---|
| 0 | 100 | 3:3:1 |
| 1 | 100 | 3:3:1 |
| 2 | 100 | 3:3:1 |
| 3 | 99 | 3:3:1 |
| 4 | 99 | 3:2.9:0.9 |
| 5 | 98 | 3:2.8:0.8 |
| 6 | 98 | 3:2.7:0.7 |

The measurement error is 5%.

The above data show that the content of modified prostaglandin $F_2$ obtained as described in example 1 decreases very slowly during accelerated storage when stored at room temperature, which is 20 degrees higher than the recommended temperature range (+4 to +8° C.) for storage of a finished cosmetic composition. However, the content of prostaglandins $E_2$ and $E_1$ decreases over time due to their transformation into other products. It should be noted that if, instead of prostaglandin $F_2$ of the invention, obtained as described in example 1, another derivative of prostaglandin $F_2$, in particular nitroprostamide $F_2$, is used in a cosmetic composition for promoting hair growth, then the latter cannot withstand storage at room temperature for 2 weeks and is completely converted into another product under mentioned conditions.

Thus, the experimental data obtained indicate high stability of the compositions based on the combination of prostaglandin derivatives of the invention.

Clinical Laboratory Studies of the Composition of the Invention for Hair Growth Clinical laboratory studies of a hair growth agent with a cosmetic formula based on three modified prostaglandins for hair (see an example of the composition above) were carried out, in particular, using two compositions including different combinations of the invention:

composition 1 included a combination of two modified prostaglandins comprised of:

150 μg/mL (0.015%) of the compound of formula (I);

50 μg/mL (0.005%) of the compound of formula (III);

in a 3:1 ratio.

composition 2 included combinations of three modified prostaglandins comprised of:

150 μg/mL (0.015%) of the compound of formula (I);

150 μg/mL (0.015%) of the compound of formula (II);

50 μg/mL (0.005%) of the compound of formula (III);

in a 3:3:1 ratio.

The experiments were carried out on 22 volunteer women aged 25 to 62 years, with female type of alopecia of varying severity.

When conducting studies, prior to the use of these formulations, all volunteers signed an informed consent to conduct of such studies and use the results obtained for scientific purposes.

Objective experimental clinical studies were carried out before and after the application of this cosmetic product with profilometry of the scalp (a thorough examination of the head and specific areas to be treated) with an assessment of a hair count per unit area using a VISIOSCAN VC 98 profilometer manufactured by Courage+Khazaka electronic GmbH (Germany).

Scalp profilometry measurements with an assessment of a hair count per unit area (density) were carried out under the same conditions both before the first measurement and after the course of application of the hair growth agent of the invention. The hair density of each volunteer was assessed in the parietal region, at a strictly defined point marked with a marker before the start of the studies, two times before and after the application of these formulations of the invention, which is reflected in the case report forms for each patient. A 16 $mm^2$ area was used on the device to calculate the hair density and scalp photographs (a photograph of the area for analysis).

The said formulations of the invention were used according to the following scheme: they were applied once a day daily in a quantity of about 1 mL of the composition on a selected area of the scalp. The duration of application was 3 months.

Compositions 1 and 2 of the invention were made in the form of a lotion and had a uniform consistency, were easily and evenly applied to the skin, were well absorbed, did not have an irritating and sensitizing effect. Significant subjective results were observed after application of hair growth compositions 1 and 2: hair acquired shine and hair loss decreased. The results of studies are shown in FIG. 1.

Data analysis and statistical processing show the following. After comparing the two formulations (compositions) of the hair growth agent with the baseline level, a significant increase in hair density was noted when applying formulation 2 with three modified prostaglandins compared to formulation 1 that contained only two modified prostaglandins, however, formulation 1 also showed good efficacy.

Thus, in the course of the studies, it was unexpectedly found that the combinations of the invention and compositions based thereon can significantly increase the total number of hairs in a subject. Thus, in particular, on the basis of analyses of phototrichograms after 3 months of using the compositions of the invention in women, the total number of hairs increases from 13 to almost 30%.

Although the invention has been described with reference to the disclosed embodiments, it will be apparent to those skilled in the art that the specific experiments described in detail are for illustrative purposes only and should not be construed as limiting the scope of the invention in any way. It should be appreciated that various modifications are possible without departing from the essence of the present invention.

The invention claimed is:

1. A combination for hair growth enhancing and/or prevention and/or treatment of alopecia in a subject, comprising at least a compound of formula (I) and a compound of formula (II) and/or formula (III), wherein the compound of formula (I) is:

Formula (I)

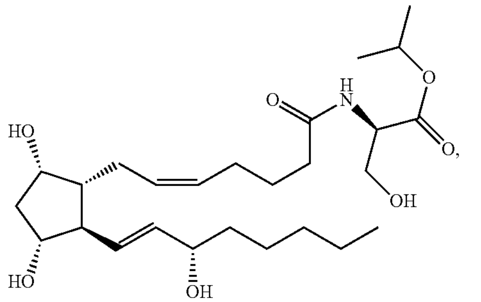

the compound of formula (II) is:

Formula (II)

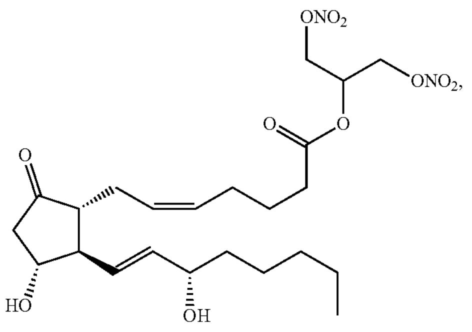

the compound of formula (III) is:

Formula (III)

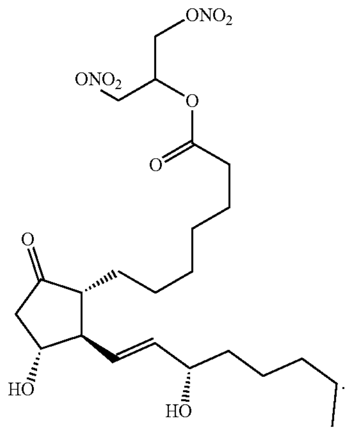

2. The combination according to claim 1, comprising a compound of formula (I), formula (II) and formula (III).

3. The combination according to claim 1, comprising a compound of formula (I) and formula (II).

4. The combination according to claim 1, comprising a compound of formula (I) and formula (III).

5. The combination according to claim 1, wherein alopecia is androgenetic, diffuse or alopecia areata.

6. A composition for hair growth enhancing and/or prevention and/or treatment of alopecia, comprising the combination according to claim 1 and at least one excipient.

7. The composition of claim 6, wherein the components of the combination are in an effective quantity.

8. The composition of claim 6, wherein the excipient is a carrier, filler and/or solvent.

9. The composition of claim 6, wherein the content of the compound of general formula (I) in the combination is 50-300 μg per 1 mL of the finished composition.

10. The composition of claim 6, wherein the content of the compound of general formula (II) in the combination is 50-300 μg per 1 mL of the finished composition.

11. The composition of claim 6, wherein the content of the compound of general formula (III) in the combination is 50-200 μg per 1 mL of the finished composition.

12. A method of hair growth enhancing and/or prevention and/or treatment of alopecia in a subject, comprising administering a composition comprising the combination according to claim 1 and at least one excipient.

13. The method according to claim 12, wherein alopecia is androgenetic, diffuse or alopecia areata.

14. The method according to claim 12, wherein the composition is applied topically.

15. The method according to claim 14, wherein the composition is applied daily or every other day.

16. The method according to claim 12, wherein the subject is a human.

* * * * *